United States Patent [19]

Sullivan et al.

[11] Patent Number: 5,893,716

[45] Date of Patent: Apr. 13, 1999

[54] DENTAL INSTRUMENT

[76] Inventors: William Sullivan, 4470 Van Cortland Park East, Bronx, N.Y. 10470; Peter J. Wilk, 185 W. End Ave., New York, N.Y. 10023

[21] Appl. No.: 09/072,839

[22] Filed: May 5, 1998

[51] Int. Cl.$^6$ .................................................. A61C 1/12
[52] U.S. Cl. ................................................... 433/130
[58] Field of Search ................................. 433/112, 114, 433/130, 133

[56] References Cited

U.S. PATENT DOCUMENTS

| | | | |
|---|---|---|---|
| 274,008 | 3/1883 | Lincoln | 433/133 |
| 522,291 | 7/1894 | Davis | 433/130 |
| 3,109,238 | 11/1963 | Marks | 433/29 |
| 4,281,989 | 8/1981 | Glover et al. | 433/130 |
| 4,303,393 | 12/1981 | Gentry | 433/130 |
| 4,673,351 | 6/1987 | Luiset et al. | 433/29 |

FOREIGN PATENT DOCUMENTS 799430  6/1936  France .................. 433/130

*Primary Examiner*—Nicholas D. Lucchesi
*Attorney, Agent, or Firm*—R. Neil Sudol; Henry D. Coleman

[57] ABSTRACT

A dental instrument includes an elongate handle having a structural axis, a drill bit mounted to the handle at a distal end thereof for rotation about a rotation axis different from and substantially parallel to the structural axis, and a drive operatively connected to the drill bit and disposed at least partially in the handle for rotating the drill bit about the rotation axis. The drill bit is part of a bit assembly detachably secured to the handle at the distal end thereof. Where the handle includes a nozzle at the distal end, the bit assembly including means for redirecting liquid from the nozzle approximately to a free end of the drill bit. This redirection component may include a deflector surface or, alternatively, a channel or passageway for repressurizing liquid from the nozzle. In the latter case, another nozzle is provided at the downstream end of the channel or passageway. In addition, it is contemplated that the bit assembly includes a mechanical power linkage releasably connected to the drive. The mechanical linkage may be permanently or removably connected to the drill bit.

9 Claims, 2 Drawing Sheets

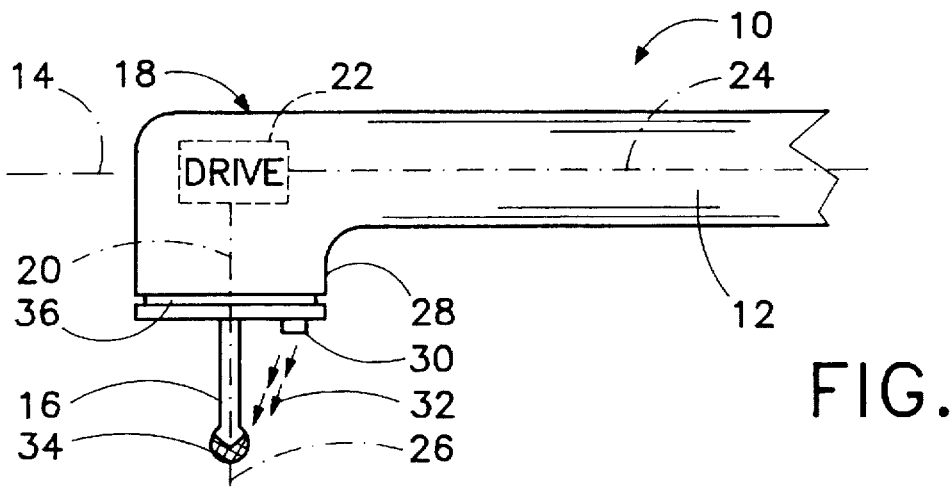
FIG. 1
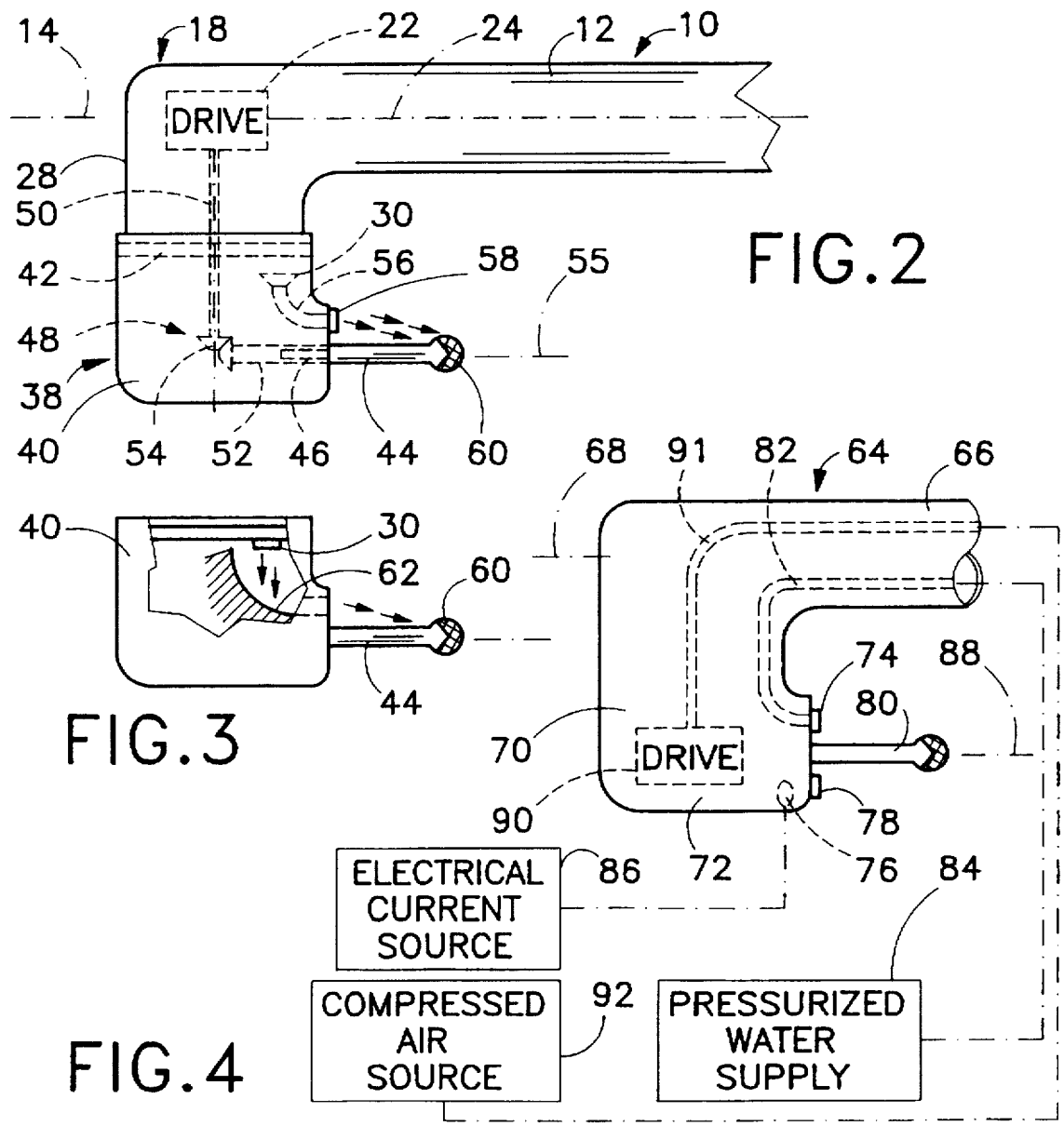
FIG. 2
FIG. 3
FIG. 4

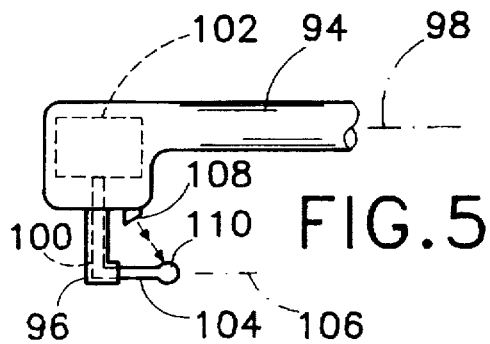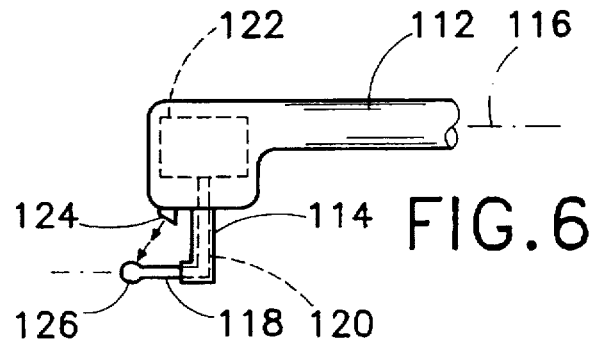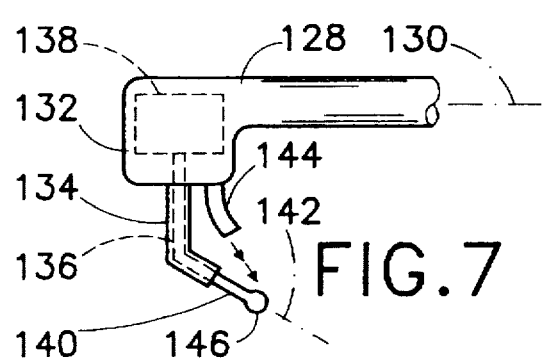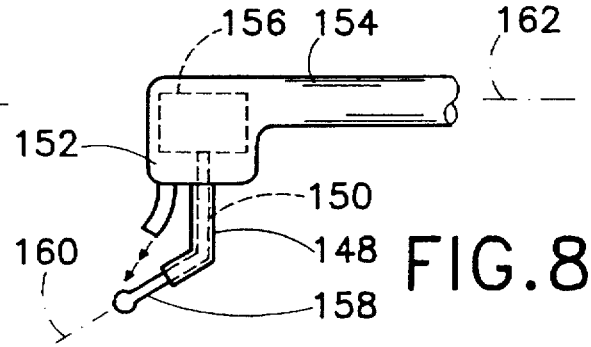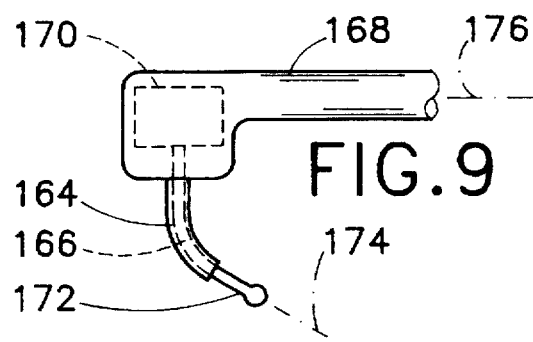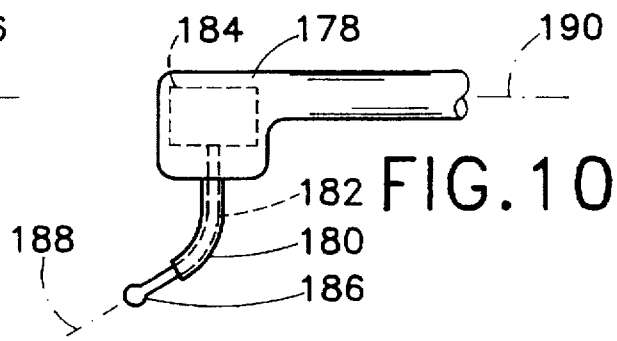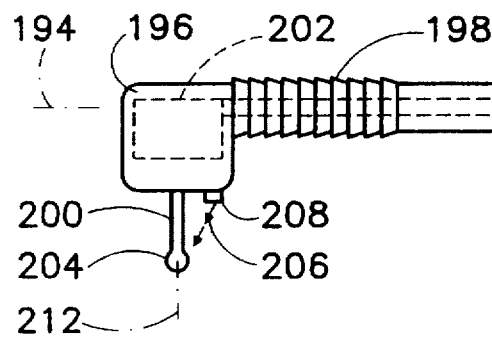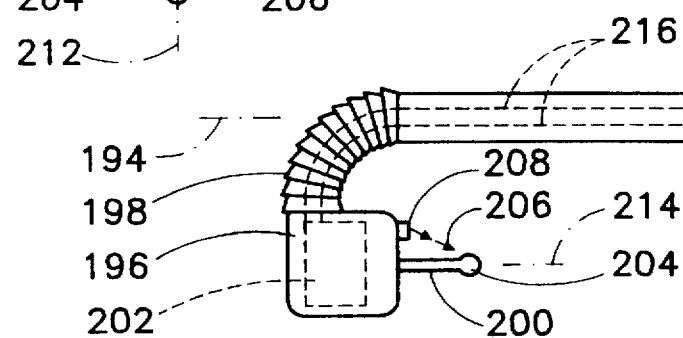

DENTAL INSTRUMENT

BACKGROUND OF THE INVENTION

This invention relates to a dental instrument. More specifically, this invention relates to a dental drill.

A continuing challenge for dentists is to obtain access to different tooth surfaces. It is particularly difficult to obtain access to lingual surfaces. Not only is it difficult to view such dental surfaces but it is difficult to operate on such surfaces.

A dental drill generally has a drill bit extending at a substantial angle (e.g., approximately 90°) relative to the handle of the instrument. In order to reach some lingual surfaces, it is necessary to push the drill handle against the patient's face. Even then, the contact of the drill bit with the tooth surface is only partially satisfactory since the angle between the tooth surface and the bit may be an acute angle.

There is a need for dental instruments which facilitate the obtaining of access to lingual tooth surface and other difficult-to-reach areas.

OBJECTS OF THE INVENTION

An object of the present invention is to provide a dental instrument which facilitates access to lingual tooth surfaces.

A more specific object of the present invention is to provide a dental drill which facilitates access to lingual tooth surfaces.

Another object of the present invention is to provide a dental drill which is adjustable for facilitating access to different tooth surfaces.

A further object of the present invention is to provide a dental drill attachment for converting a standard dental drill instrument to an instrument adapted for lingual access.

These and other objects of the present invention will be apparent from the drawings and descriptions herein.

SUMMARY OF THE INVENTION

A dental instrument in accordance with the present invention comprises an elongate handle having a structural axis, a drill bit mounted to the handle at a distal end thereof for rotation about a rotation axis different from and substantially parallel to the structural axis, and a drive operatively connected to the drill bit and disposed at least partially in the handle for rotating the drill bit about the rotation axis.

In accordance with another feature of the present invention, the drill bit is part of a bit assembly detachably secured to the handle at the distal end thereof Where the handle includes a nozzle at the distal end, the bit assembly including means for redirecting liquid from the nozzle approximately to a free end of the drill bit. This redirection component may include a deflector surface or, alternatively, a channel or passageway for repressurizing liquid from the nozzle. In the latter case, another nozzle is provided at the downstream end of the channel or passageway. In addition, it is contemplated that the bit assembly includes a mechanical power linkage releasably connected to the drive. The mechanical linkage may be permanently or removably connected to the drill bit.

In accordance with a further feature of the present invention, the handle is provided at the distal end with an extension projecting from one side of the handle away from the structural axis, the drill bit being mounted to the extension. The extension may be permanently connected to the handle and may incorporate a nozzle for directing liquid approximately to a free end of the drill bit, as well as a source or light outlet for directing light approximately to a free end of the drill bit.

Pursuant to an additional feature of the present invention, the handle is provided at the distal end with a permanent extension to which the drill bit is mounted. The extension is adjustably coupled to the handle so that an orientation of the rotation axis relative to the structural axis can be adjusted. This adjustability may be implemented by a gooseneck handle portion connected to the extension. The handle may be provided with a manually releasable locking mechanism for holding the gooseneck in a desired configuration.

The present invention is also directed to a dental attachment utilizable with a dental drill handle having a structural axis and a drive for rotating a drill bit about a first rotation axis oriented at a substantial angle relative to the structural axis of the handle. The attachment comprises a frame or body, a first connector on the frame or body for removably attaching the frame or body to a distal end of the dental drill handle, a second connector disposed on the frame or body at a point spaced from the first connector for coupling a drill bit to the frame or body, and a mechanical power transmission coupling in the frame or body for transmitting rotary power from the drive in the handle to the drill bit coupled to the frame or body via the second connector.

Where the handle includes a nozzle, the attachment further comprising means in the frame or body for redirecting liquid from the nozzle approximately to a free end of the drill bit. That redirecting element may a deflector surface or a channel for repressurizing liquid from the nozzle.

A dental drill and an attachment in accordance with the present invention facilitate the practice of dentistry by increasing access by a dental drill to lingual and other marginally accessible oral surfaces.

BRIEF DESCRIPTION OF THE DRAWINGS

FIG. 1 is a schematic side elevational view of a dental drill instrument in accordance with the present invention.

FIG. 2 is a schematic side elevational view similar to FIG. 1, showing an attachment or adapter connected to the dental instrument of FIG. 1.

FIG. 3 is a schematic side elevational view, partially broken away, depicting a modification of the attachment or adapter of FIG. 2.

FIG. 4 is partially a partial schematic side elevational view and partially a block diagram of a dental instrument in accordance with the present invention.

FIG. 5 is a partial schematic side elevational view of another dental instrument in accordance with the present invention.

FIG. 6 is a partial schematic side elevational view of a further dental instrument in accordance with the present invention.

FIG. 7 is a partial schematic side elevational view of an additional dental instrument in accordance with the present invention.

FIG. 8 is a partial schematic side elevational view of an alternative dental instrument in accordance with the present invention.

FIG. 9 is a partial schematic side elevational view of a supplemental dental instrument in accordance with the present invention.

FIG. 10 is a partial schematic side elevational view of yet another dental instrument in accordance with the present invention.

FIGS. 11A and 11B are partial schematic side elevational views of an adjustable dental instrument in accordance with the present invention, showing the instrument in two alternate configurations.

DESCRIPTION OF THE PREFERRED EMBODIMENTS

As illustrated in FIG. 1, a hand-held dental instrument 10 has an elongate handle 12 which is generally symmetric about a longitudinal structural axis 14. A drill bit 16 is mounted to a distal end 18 of the instrument 10 and is operatively connected to a drive 22 either directly or indirectly via a drive shaft 20. Drive 22 takes a conventional form such as a turbine powered via compressed air delivered to the turbine via a supply line 24. Upon the feeding of compressed air to drive turbine 22, the turbine rotates drill bit 16 about a rotation axis 26 which extends at an approximately 90° angle to structural axis 14.

A head 28 at the distal end 18 of instrument handle 12 is provided with a nozzle 30 for dispensing a liquid 32 such as water towards a burr 34 at the free end of drill bit 16. Head 28 is also provided with a groove 36 for removably connecting an attachment or adapter 38 (FIG. 2) to the instrument of FIG. 1. Attachment or adapter 38 includes a frame or body member 40 which is provided on one side with an internal thread or ridge 42 for releasably mating with groove 36 to connect the attachment or adapter to head 28 of instrument 10.

A drill bit 44 is permanently or removably coupled, e.g., via male-female connector elements 46, to body member 40 and particularly to a mechanical drive train 48 which is operatively connectable to turbine 22. Drive train 48 includes a pair of shafts 50 and 52 coupled via beveled gears 54 and serves to rotate drill bit 44 about a rotation axis 55 oriented substantially parallel to structural axis 14.

Body member 40 is additionally provided with a tapered channel or passageway 56 for directing water from nozzle 30 to an auxiliary nozzle 58 and for increasing the pressure of the liquid. Nozzle 58 directs a spray or jet of water to a burr 60 of drill bit 44.

FIG. 3 depicts a modification of the attachment or adapter 38 of FIG. 2. Instead of channel or passageway 56, body member 40 is provided with a deflector surface 62 which guides a stream of water from nozzle 30 towards burr 60.

As illustrated in FIG. 4, a dental instrument 64 has an elongate handle 66 extending about a structural axis 68 and provided at a distal end with an extension 70 projecting away from handle 66 and axis 68, substantially perpendicularly thereto. Extension 70 is formed at a free end with a head 72 which carrier an irrigation or spray nozzle 74, a light source or lamp 76, with a lens 78, and a drill bit 80. Irrigation or spray nozzle 74 is connected via a duct or hose 82 to a pressurized water supply 84. Light source or lamp 76 is energized by an electrical current source 86. Drill bit 80 is turned about a rotation axis 88 by a drive turbine 90 connected via a hose 91 to a compressed air source 92. Rotation axis 88 is oriented substantially parallel to axis 68 of handle 66.

FIGS. 5 through 10 illustrate variations of the design of FIG. 4. As shown in FIG. 5, a handle 94 is provided at a distal end with a sleeve 96 extending perpendicularly to an axis 98 of handle 94. Sleeve 96 houses a mechanical drive train 100 which transmits rotary power from an air-driven turbine 102 to a drill bit 104 to rotate the drill bit about an axis 106 extending parallel to axis 98. A nozzle 108 dispenses water towards a burr 110 at the free end of drill bit 104.

FIG. 6 shows a dental instrument including a handle 112, a sleeve 114 extending right angles to an axis 116 of the handle, a drill bit 118 mounted to a mechanical drive train 120 disposed in the sleeve 114 and coupled at an upstream side to a drive turbine 122. A nozzle 124 ejects irrigation fluid towards a burr 126 at a free end of drill bit 118. Drill bit 118 points in a forward or distal direction relative to handle 112, in contrast to drill bit 104 which extends in a proximal direction back towards the user along the respective handle 94.

As depicted in FIG. 7, a dental drill instrument comprises an elongate handle 128 having a structural axis 130 and a head 132 carrying an angled sleeve 134. Sleeve 134 encloses a mechanical drive train 136 for transmitting rotary power from a drive turbine 138 in head 132 to a drill bit 140 extending substantially parallel to axis 130. More specifically, drill bit 140 extends along a rotation axis 142 at an angle of 45° or less relative to axis 130. A nozzle member 144 sprays water or other liquid towards a burr 146 at the free end of drill bit 140.

FIG. 8 illustrates a dental drill instrument in which an angled sleeve 148 containing a mechanical power transmission train 150 projects laterally from a head 152 at a distal end of an instrument shaft or handle 154. Sleeve 148 is angled in a forward or distal direction as opposed to sleeve 134 which is angled towards the rear or in a proximal direction. Train 150 carries rotary power from a drive turbine 156 to a drill bit 158 so that the drill bit spins about a rotation axis 160 which is oriented substantially parallel (less than 45°) to an axis 162 of handle 154.

According to FIG. 9, an arcuate sleeve 164 encasing a flexible drive shaft 166 projects laterally and in a proximal direction relative to an instrument handle 168. Drive shaft 166 is connected at an upstream end to a drive turbine 170 and at a downstream end to a drill bit 172 for rotating the drill bit about an axis 174 oriented substantially parallel (less than 45°) to an axis 176 of instrument handle 168.

FIG. 10 concerns a dental instrument having a handle 178 provided at a distal end with an arcuate sleeve 180 projecting laterally an in a forward direction from handle 178. Sleeve 180 houses a flexible power transmission element 182 which conveys rotary power from a drive turbine 184 to a drill bit 186 to revolve the bit about a rotation axis 188 oriented substantially parallel to an axis 190 of handle 178.

As illustrated in FIGS. 11A and 11B, a dental drill instrument comprises a handle 192 having a structural axis 194. A head 196 is adjustably coupled to a distal end of handle 192 via a gooseneck section 198. A drill bit 200 is removably connected to a drive turbine 202 in head 196 and carries a burr 204 which is cooled by a water spray 206 from a nozzle 208 in head 196. A knob 210 is provided on handle 192 at a proximal end thereof for releasably locking gooseneck section 198 in a desired configuration thereby locking head 196 and drill bit 200 in desired positions relative to handle 192. As shown in FIG. 11A, gooseneck section 198 has a linear configuration so that drill bit 200 rotates, under the action of turbine 202, about an axis 212 oriented substantially perpendicularly relative to handle axis 194. FIG. 11B shows an arcuate configuration of gooseneck section 198 so that drill bit 200 rotates about an axis 214 oriented substantially parallel to axis 194. Knob 210 is connected to tensile locking elements 216 which are connected also to head 196.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that there are other techniques for adjustably attaching a head to a shaft or handle of a dental instrument which are equivalent to the gooseneck 198 of FIGS. 11A and 11B. Such an equivalent structure might be a hinge, for example.

Accordingly, it is to be understood that the drawings and descriptions herein are proferred by way of example to facilitate comprehension of the invention and should not be construed to limit the scope thereof.

What is claimed is:

1. A dental instrument comprising:

an elongate handle having a structural axis;

a rotary drive detachably receiving a first drill bit, said rotary drive being disposed at least partially in said handle for rotating said drill bit about a first rotation axis oriented at a non-zero first angle relative to said structural axis in a plane including said structural axis;

a drill bit holder mountable to said handle at a distal end thereof for operatively connecting a second drill bit to said drive to enable rotation thereof about a second rotation axis oriented at a second angle to said structural axis, said second angle being less in magnitude than said first angle; and mounting means on said drill bit assembly and said drill bit holder for removably connecting said drill bit holder to said handle.

2. The instrument defined in claim 1 wherein said handle includes a spray nozzle at said distal end aimed at a free end of said first drill bit when said first drill bit is attached to said handle at said distal end thereof, said drill bit holder including means for redirecting liquid from said nozzle approximately to a free end of said second drill bit when said second drill bit is attached to said drill bit holder and said drill bit holder is mounted to said handle.

3. The instrument defined in claim 2 wherein said means for redirecting includes a deflector surface.

4. The instrument defined in claim 2 wherein said means for redirecting includes a channel or passageway for repressurizing liquid from said nozzle.

5. The instrument defined in claim 1 wherein said drill bit holder includes a mechanical power linkage releasably connected to said drive.

6. The instrument defined in claim 5 wherein said mechanical linkage is permanently connected to said second drill bit.

7. The instrument defined in claim 1 wherein said angle is less than approximately 10°.

8. The instrument defined in claim 1 wherein said handle is provided with locking means for holding said gooseneck in a desired configuration.

9. A dental instrument comprising:

an elongate handle having a structural axis and, at a distal end, an adjustably bendable gooseneck portion;

a drill bit mounted to said gooseneck portion for rotation about a rotation axis oriented at an angle to said structural axis; and a drive operatively connected to said drill bit and disposed at least partially in said handle for rotating said drill bit about said rotation axis.

* * * * *